United States Patent [19]

Steffee

[11] Patent Number: 4,719,905
[45] Date of Patent: * Jan. 19, 1988

[54] APPARATUS AND METHOD FOR MAINTAINING VERTEBRAE IN A DESIRED RELATIONSHIP

[75] Inventor: Arthur D. Steffee, Moreland Hills, Ohio

[73] Assignee: AcroMed Corporation, Cleveland, Ohio

[*] Notice: The portion of the term of this patent subsequent to Mar. 10, 2004 has been disclaimed.

[21] Appl. No.: 936,314

[22] Filed: Dec. 1, 1986

Related U.S. Application Data

[63] Continuation of Ser. No. 793,901, Nov. 1, 1985, Pat. No. 4,648,388.

[51] Int. Cl.⁴ ............................................. A61F 5/04
[52] U.S. Cl. .................................. 128/69; 128/92 ZW
[58] Field of Search ............. 128/69, 92 ZW, 97 YM; 623/17

[56] References Cited

U.S. PATENT DOCUMENTS 4,483,334 11/1984 Murray ................................. 128/69
4,611,580 9/1986 Wu ...................................... 128/69

FOREIGN PATENT DOCUMENTS 2649042 9/1978 Fed. Rep. of Germany ........ 128/89
3032237 3/1982 Fed. Rep. of Germany ........ 128/92 YM
2031508 4/1980 United Kingdom .......... 128/92 ZW Primary Examiner—Edgar S. Burr
Assistant Examiner—Tonya Lamb
Attorney, Agent, or Firm—Tarolli, Sundheim & Covell

[57] ABSTRACT

An apparatus and method is provided to maintain vertebrae in a desired relationship. The apparatus includes a rod, a plurality of clamps, and a plurality of fastener assemblies. The method invovles inserting threaded members into openings in a displaced vertebra and at least one vertebra on each side of the displaced vertebra. A clamp is placed on each fastener. The rod is bent to correspond to a desired spinal curvature and inserted into the clamps. A nut is tightened on each threaded member to hold the clamp to each vertebra and to press the clamp against the rod to hold the rod against axial and rotational movement.

13 Claims, 9 Drawing Figures

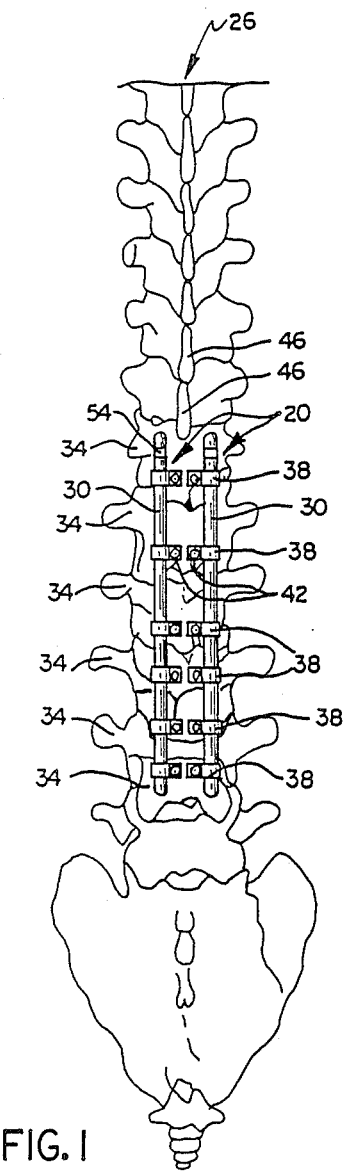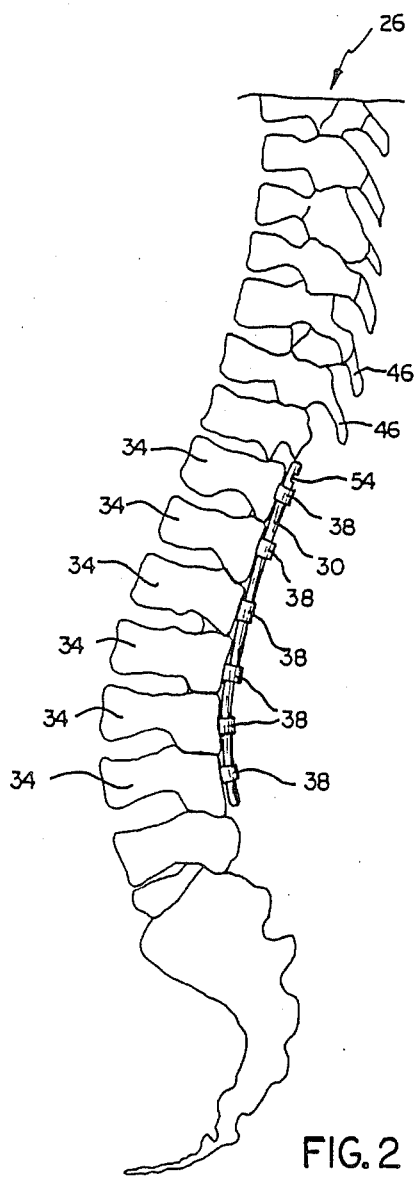
FIG. 1
FIG. 2

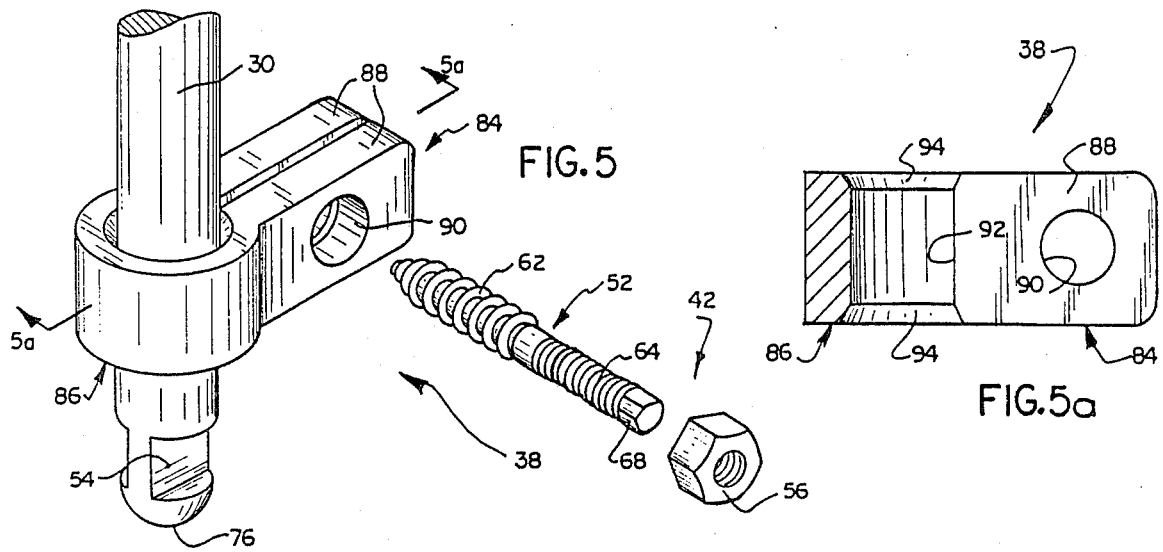
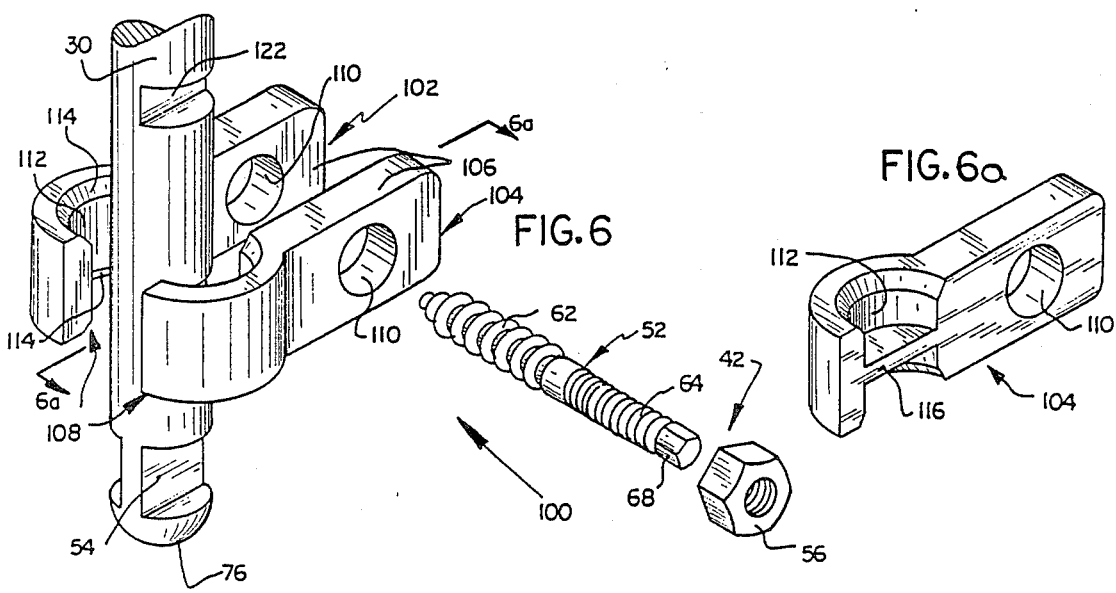
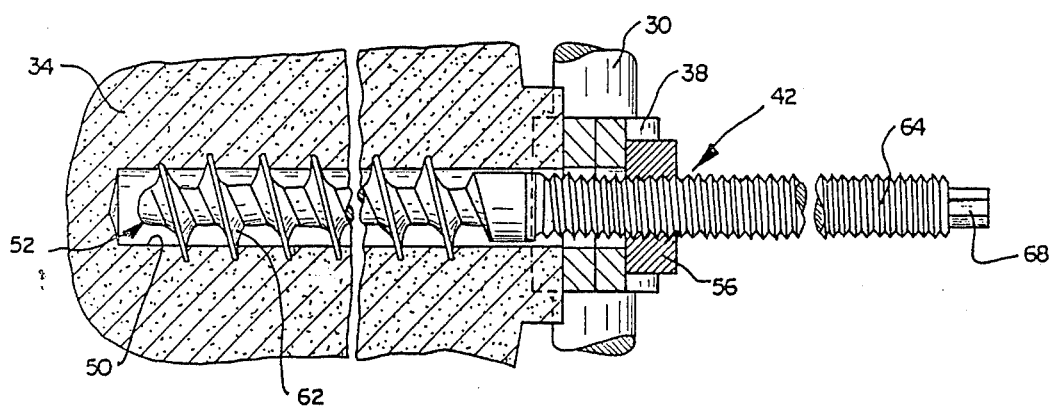

APPARATUS AND METHOD FOR MAINTAINING VERTEBRAE IN A DESIRED RELATIONSHIP

This is a continuation of co-pending application Ser. No. 793,901, now U.S. Pat. No. 4,648,388, filed on Nov. 1, 1985.

BACKGROUND OF THE INVENTION

The present invention generally relates to the correction of spinal deformities. Specifically, the present invention provides an improved apparatus and method for maintaining vertebrae in a desired spatial relationship.

Devices for correcting spinal column deformities are known. One such device is disclosed in U.S. Pat. No. 3,997,138 which has a pair of flexible rods or cables to maintain the position of adjacent vertebrae. The thin rods or cables are secured to fasteners connected with vertebrae.

Devices that include rigid plates are also known for the straightening of spinal deformities. The plates are relatively heavy and cannot be easily bent to have a curvature corresponding to the desired curvature of a particular spinal column. In addition, the rigid plates do not permit flexibility in locating the fasteners in the vertebrae.

Another known device for correcting spinal deformities includes a straight ratchet rod. The rigid ratchet rod applies compressive force to the spinal column when attached to vertebrae by hooks connected to the rod. This device does not conform to curves in the spine and only functions to compress the spine.

In another device, the corrective forces are generated by two steel rods which are wired around the spine. The rods may be bent to a desired curvature. The rods are not directly attached to all the vertebra that the rods span. Maintaining a desired spatial relationship between the vertebrae spanned by the rods is, at best, difficult.

Another known corrective device is disclosed in U.S. Pat. No. 4,041,939. The device includes a plurality of plates. Each of the plates is secured over one end of a vertebra. Fasteners are connected to the vertebrae through the plates. A cable is then crimped in the head of the fastener to attach the cable to one vertebra. Tension is put on the cable while it is crimped to an adjacent vertebra until the desired correction is accomplished. This device can only put compressive forces on the spine so that the cables are always in tension. Once the cable is crimped in place, no further adjustment between the crimped fastener and cable is possible.

SUMMARY OF THE INVENTION

The present invention provides an improved apparatus and method to maintain vertebrae in a desired relationship. When the apparatus is to be installed on a person's spinal column, force transmitting members are mounted in openings formed in the vertebrae. Base portions of clamps are connected with the fasteners. A rod is bent to the desired curvature of the spine. The bent rod is guided through each clamp. Nuts are then tightened on the force transmitting members against the clamps to grip the rod and hold it from axial and rotational movement relative to the vertebrae.

BRIEF DESCRIPTION OF THE DRAWINGS

Further features of the present invention will become apparent to those skilled in the art to which the invention relates from a reading of the following specification with reference to the accompanying drawings, in which:

FIG. 1 is a dorsal view of a portion of a spinal column with an apparatus constructed in accordance with the present invention installed to maintain a desired relationship of the vertebrae;

FIG. 2 is a sagittal view of the spinal column in FIG. 1 illustrating how the apparatus of the present invention conforms to the curvature of the spine;

FIG. 5 is a partially exploded fragmentary perspective view illustrating a clamp, rod and fastener of the apparatus of FIGS. 1 and 2;

FIG. 5a is a partial cross sectional view, taken generally along the line 5a—5a of FIG. 5, illustrating the clamp with the rod removed;

FIG. 6 is a partially exploded fragmentary perspective view illustrating a two-piece clamp, rod, and fastener of a second embodiment of the invention;

FIG. 6a is a perspective view, taken generally along the line 6a—6a of FIG. 6, illustrating one-half of the clamp with the rod removed; and FIG. 7 is an enlarged fragmentary cross sectional view illustrating how the clamp and rod are connected with a vertebra by the fastener.

DESCRIPTION OF SPECIFIC PREFERRED EMBODIMENTS OF THE INVENTION

Generally

Figure 3:
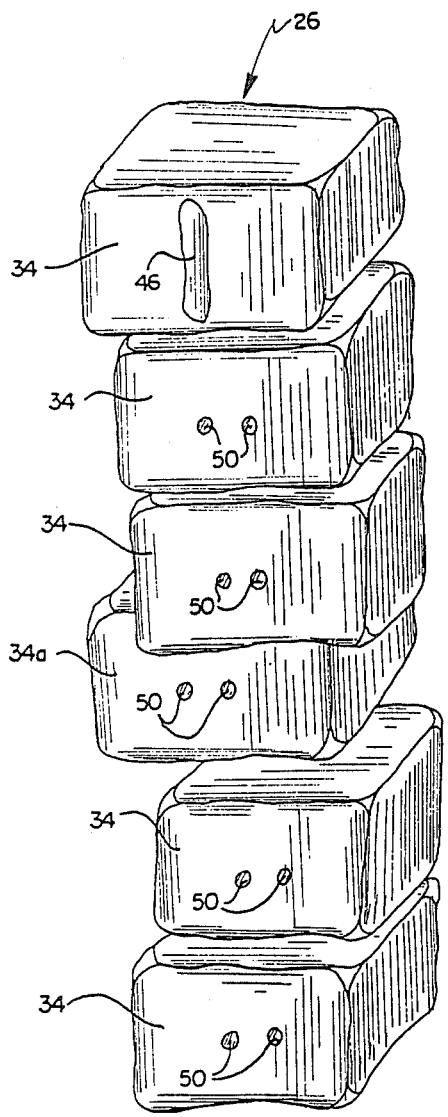
FIG. 3 is an enlarged schematic illustration of a spinal column having a displaced vertebra.

A pair of assemblies 20 for maintaining a desired relationship between adjacent vertebrae is illustrated in FIG. 1 installed on a human spinal column 26. Each of the assemblies 20 includes an elongated rod 30 connected with vertebra 34 by clamps generally designated 38 and fastener assemblies 42.

The rod 30 is connected with the spinal column 26 to hold the vertebrae 34 in the desired spatial relationship with each other. This spatial relationship is shown in FIGS. 1 and 2. To enable the rod 30 to position vertebrae in the desired relationship with each other, the rod 30 must have a length sufficient to span at least three adjacent vertebrae 34. In the illustrated embodiment of the invention, the rod 30 spans six vertebrae 34.

In order to obtain and maintain the desired spinal curvature shown in FIG. 2, the rods 30 are bent to correspond to this curvature. The rods 30 have sufficient rigidity to maintain a configuration to which they are bent when the rods are resisting movement of one or more vertebrae back to deformed positions. In one specific embodiment of the invention, the rods 30 were formed of surgical grade stainless steel and had a diameter of approximately 0.25 inches.

Once the rods 30 have been plastically deformed or bent to the desired shape, they are inserted into clamps 38 which are held on the vertebrae by fastener assemblies 42. The fastener assemblies 42 are tightened, which presses the clamp 38 against the rod 30 to prevent the rod from rotational or axial movement. The position of the rod 30 can be adjusted, if so desired, by loosening the fastener assemblies 42. Once this has been done, the rods are moved to the desired position. The fastener assemblies are retightened to again firmly grip the rod.

Figure 4:
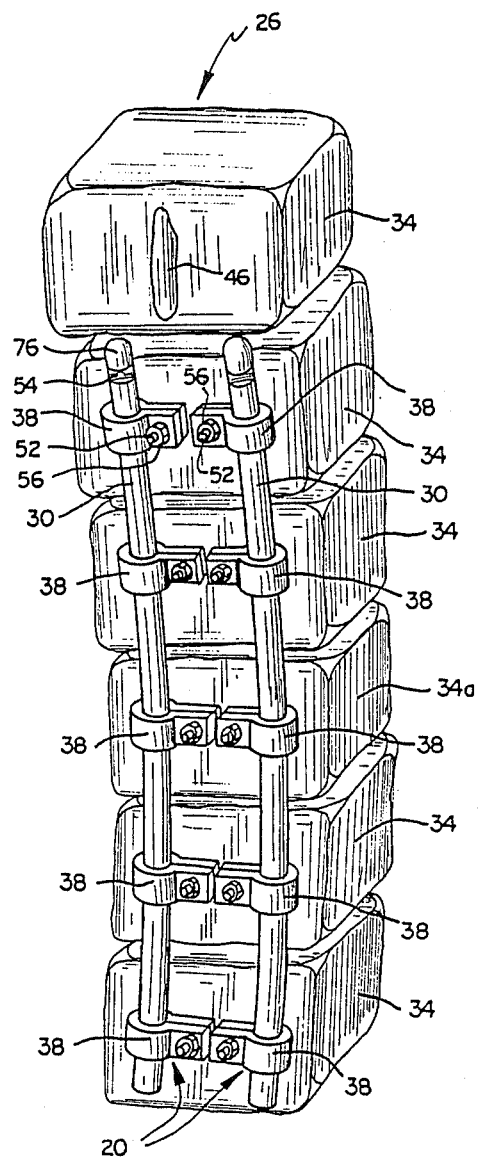
FIG. 4 is an enlarged schematic illustration, similar to FIG. 3, illustrating how the vertebrae of FIG. 3 are held in a desired relationship by the apparatus of FIGS. 1 and 2.

Prior to installing the assemblies 20, a vertebra 34a (FIG. 3) is out of place relative to adjacent vertebrae 34 which are in their normal positions. The assemblies 20 (FIG. 4) are installed to maintain the vertebrae 34 in a desired relationship in the spinal column 26.

Before the assemblies 20 are to be installed, it is necessary to determine if the spinous processes 46 (FIGS. 1-4) which project from the vertebrae 34 are to be removed. If it is determined that the spinous processes 46 will interfere with the installation of the assemblies 20, the spinous processes must be removed. If it is determined that the spinous processes 46 will not interfere with the installation of the assemblies 20, the spinous processes can be left on the vertebrae 34. The spinous processes 46 (FIG. 3) are illustrated as having been removed to allow the installation of the assemblies 20.

A pair of holes 50 (FIG. 3) for receiving part of the fastener assemblies 42 are drilled in each vertebra 34 that will be spanned by rods 30. The holes 50 are drilled so that they will be in vertical alignment with holes drilled in the adjacent vertebra 34 when the vertebrae are in the desired relationship. Force transmitting members 52 (FIG. 7) are threaded into the holes 50.

Clamps 38 (FIG. 4) for holding the rod 30 relative to the vertebra 34 are inserted over each force transmitting member 52. The clamps 38 are left loose on the force transmitting members 52. The rods 30 are bent to have a curvature corresponding to the desired curvature of the spinal column 26. The displaced vertebra 34a is held in the desired position relative to the adjacent vertebra while the bent rods 30 are inserted into the clamps 38.

A tool (not shown) is placed on a flat portion 54 of the rod 30. The tool prevents the rod 30 from rotating as the clamps 38 are tightened around the rod. To position and tighten a clamp 38, a nut 56 is threaded onto each of the force transmitting members 52 and tightened against the clamp to press the clamp to a vertebra 34. As the nut 56 is tightened, the clamp 38 also firmly grips the rod 30.

Fastener

The fastener assembly 42 (FIG. 7) connects a clamp 38 with a vertebra 34 and closes the clamp against a rod 30. The fastener assembly 42 includes a force transmitting member 52 (FIGS. 5 and 7) having a first threaded portion 62 and a second threaded portion 64. The first threaded portion 62 has a relatively large diameter helix for threading into a hole 50 in a vertebra 34. The first threaded portion 62 has a substantially larger crest diameter than the inside diameter of the hole 50.

As the first threaded portion 62 is threaded into the hole 50, the helix cuts into the cylindrical side surface of the hole 50 to firmly attach force transmitting member 52 the vertebra 34. The force transmitting member 52 is threaded into the vertebra 34 by placing a tool (not shown) on the hex head portion 68. The tool and force transmitting member are then rotated until the desired depth of engagement with the vertebra 34 is obtained. The force transmitting member 52 is made from a surgical grade stainless steel or titanium.

The second threaded portion 64 of the force transmitting member 52 has a standard external screw thread for engaging a standard internal thread in a nut 56. The nut 56 has a standard hexagonal external configuration for a suitable tool to engage and rotate the nut relative to the second threaded portion 64. The nut 56 is rotated until it abuttingly engages clamp 38. Rotation of the nut 56 is continued until the clamp 38 is pressed solidly against the vertebra 34 and the rod 30 is firmly clamped in place. After the nut 56 is rotated to its final desired position, the threaded portion 64 that extends beyond the nut 56 is trimmed off adjacent to the nut. The force transmitting member 52 has the same general construction disclosed in U.S. patent application Ser. No. 562,438, now U.S. Pat. No. 4,611,581, filed Dec. 16, 1983 for "Apparatus for Straightening Spinal Columns", by Arthur D. Steffee.

Rod

The cylindrical rod 30 interconnects and holds a plurality of vertebrae in a desired spatial relationship. Before the rod 30 is installed in the clamps 38, the rod is bent to have a curvature corresponding to the desired curvature of the spinal column 26 (see FIG. 2). The bent rod 30 has sufficient rigidity to maintain its curvature and hold the vertebrae in place.

The rod 30 has rounded ends 76. The rounded ends 76 allow the rod 30 to be easily inserted through the clamps 38 during installation. The rounded ends 76 also serve to prevent the rod 30 from damaging nearby tissue or bone that it may contact after installation.

The rod 30 also has at least one portion with flats 54 in the rod. The flat portion 54 is gripped with a suitable tool to prevent the rod 30 from rotating about its axis when the clamps 38 are fastened around the rod to hold the rod in a desired position.

Clamp—First Embodiment

The one-piece clamp 38 (FIG. 5) holds a rod 30 against rotational and axial movement relative to a vertebra. The one-piece clamp 38 has a base portion 84 and a clamp portion 86. The base portion 84 has two legs 88 extending from the clamp portion 86. The legs 88 are slightly spaced apart and the clamp portion 86 has a small resilient force acting to keep the legs spaced. Each of the legs 88 has a circular opening 90 for receiving the force transmitting member 52. The clamp portion 86 (FIG. 5a) has an arcuate wall inner surface 92 of a generally cylindrical configuration extending around most of the rod 30 for engaging and clamping a portion of the rod which is disposed in the clamp 38. The legs 88 extend from end portions of the inner surface 92.

In its free state, the inner surface 92 has an inner diameter slightly larger than the outer diameter of the rod 30. The legs 88 are resiliently pressed together by tightening nut 56 against the base portion 84. The tightening of nut 56 also reduces the inner diameter of the inner surface 92 slightly to firmly grip the rod 30 to hold the rod against axial and rotational movement. The clamp portion 86 has a pair of frustoconical surfaces 94 coaxially connected to inner surface 92 with their bases extending outward. The frustoconical surfaces 94 enable the rod 30 to be easily inserted in the clamp portions 86 during installation.

The rod 30 is thereby maintained in the installed position due to the clamping force exerted around the rods by the inner surface 92 when the nut 56 is tightened to engage base portion 84. If any subsequent correction of the vertebrae is required, the clamps can be loosened to permit repositioning or replacement of the rod 30.

Clamp and Rod—Second Embodiment

A two-piece clamp 100 is illustrated in FIG. 6. The two-piece clamp 100 is made up of halves 102 and 104. Each half 102 or 104 has a base portion 106 and a clamp portion 108. The base portion 106 of each half 102 or 104 has an opening 110 for receiving the force transmitting member 52.

The clamp portion 108 of half 102 has a semi-circular surface 112 and partial frustoconical surfaces 114. Frustoconical surfaces 114 are coaxial with arcuate surface 112, and have their bases extending outwardly.

The clamp half 104 (FIG. 6a) has a web or tang 116 extending inwardly from the arcuate surface 112. The web 116 extends into a notch 122 (FIG. 6) in the rod 30. The web 116 and notch 122 cooperate to prevent axial and rotational movement of the rod 30 relative to the vertebrae 34 during and after installation. The arcuate surfaces 112 of halves 102, 104 form a generally cylindrical configuration when they are installed.

The rod 30 has a plurality of the notches 122 spaced along the length of the rod. The distance between notches can be varied to accommodate different distances between vertebrae 34 as would be encountered with patients having different frame sizes.

The installation of the two-piece clamp 100 and rod 30 with notches 122 is slightly different than the one-piece clamp 82. Once both halves 102, 104 of the two-piece clamp 100 are installed on the fasteners 42, the bent rod 30 is not threaded into the clamp. The halves 102, 104 merely are separated a sufficient distance to allow the rod 30 to be fitted laterally in between the halves. Once this is done at each vertebra 34, the nut 56 can be tightened against the clamp 100. The rod 30 has a flat portion 54 for maintaining an exact desired position of the rod during installation. Once the nuts 56 have been tightened, the tang 116 and the notch 122 cooperate to prevent any rotational or axial movement of the rod 30 relative to the vertebrae 34.

Conclusion

The present invention provides an improved assembly 20 (FIG. 1) and method for maintaining vertebrae 34 in a desired relationship. The assembly 20 includes a rod 30, clamps generally designated 38, and fastener assemblies 42.

Force transmitting members 52 are threaded into openings 50 in the vertebrae 34. Clamps 38 are put on the force transmitting members 52. A rod 30 is bent to a configuration which will maintain the vertebrae 34 in a desired relationship. The rod 30 is inserted into clamps 38. The rod 30 is held in place while nuts 56 are tightened to secure the clamps 38 to the vertebrae 34, and to press the clamps 38 against the rod 30.

Having described specific preferred embodiments of the invention, the following is claimed:

1. An apparatus for maintaining vertebrae in a desired relationship, said apparatus comprising:
    a rod, said rod being deformable to a configuration which is a function of a desired curvature of a spine, said rod having a sufficient length and rigidity to maintain the vertebrae in the desired relationship;
    clamp means for gripping a portion of said rod, said clamp means having a clamp portion which includes inner surfaces which circumscribe said rod, said clamp means also having a base portion projecting outwardly from one side of said clamp portion, said base portion includes surface means defining an opening which is offset to one side of said rod; and
    fastener means for securing said clamp means to a vertebra and for pressing said inner surfaces of said clamp means against an outer side surface of said rod to hold said rod against axial and rotational movement relative to said clamp means, said fastener means including an externally threaded member extending through the opening in said base portion and having a central axis extending transversely to a central axis of said rod, said externally threaded member including threads for engaging a vertebra disposed on a first side of said clamp means.

2. An apparatus as set forth in claim 1 wherein said fastener means includes second thread means extending outwardly of a second side of said clamp means, and internally threaded means for engaging said second thread means and applying force against said clamp means to press said clamp means against the vertebra engaged by said first thread means.

3. An apparatus as set forth in claim 1 wherein said rod has a circular cross section configuration, said rod having at least one end portion with flats thereon for engagement by a tool to prevent said rod from rotating about its axis during the installation of said rod in said clamp means.

4. An apparatus as set forth in claim 1 wherein said clamp portion of said clamp means includes an arcuate wall for extending at least part way around said rod, said arcuate wall having first and second end portions which are disposed adjacent to each other and are offset to one side of said rod, said base portion of said clamp means including a first leg section extending outwardly from said first end portion of said arcuate wall, a second leg section extending outwardly from said second end portion of said arcuate wall and disposed in a side-by-side relationship with said first leg section, said surface means defining an opening in said base portion including a first surface extending through said first leg section to form a first opening and a second surface extending through said second leg section to form a second opening, said first and second openings being disposed in a coaxial relationship.

5. An apparatus as set forth in claim 4 wherein said arcuate wall includes a first arcuate section connected with said first leg section and a second arcuate section connected with said second leg section and separate from said first arcuate section, said first arcuate section of said wall and said first leg portion being pressed against the vertebra engaged by said first thread means, said second arcuate section of said wall and said second leg section being formed separately from said first arcuate section of said wall and said first leg section and being spaced from the vertebra engaged by said first thread means.

6. An apparatus as set forth in claim 5 wherein one of said arcuate sections of said arcuate wall has an inwardly projecting tang portion, said rod having a plurality of spaced apart notches which extend partially through said rod and transversely to the axis of said rod for receiving said tang portion to prevent rotational and axial movement of said rod relative to said clamp means.

7. An apparatus as set forth in claim 4 wherein said arcuate wall and said first and second leg sections are formed as one piece, said fastener means including means for urging said first and second leg section toward each other to press said arcuate wall against the outer side surface of said rod.

8. A method of maintaining vertebrae in a desired relationship, said method comprising:
    drilling at least one opening in a displaced vertebra;
    drilling an opening in a vertebra disposed on a first side of the displaced vertebra;
    drilling an opening in a vertebra disposed on a second side of the displaced vertebra;
    placing base portions of clamps onto fasteners;

threading the fasteners into the openings in the vertebrae;

bending at least one rod to a curvature corresponding to the desired relationship of the vertebrae;

inserting the bent rod into the clamps while maintaining the curvature of the rod; and holding the rod against axial and rotational movement while tightening the fasteners against the clamps to grip the rod while maintaining the curvature of the rod.

9. A clamp for use with an apparatus for maintaining vertebrae in a predetermined relationship wherein the apparatus includes at least one fastener for securing the clamp to a vertebra and a cylindrical rod, said clamp comprising:

a clamp portion having inner surface means for circumscribing a portion of the rod; and a base portion extending from said clamp portion and having surface means defining an opening through said base portion for receiving the fastener, said opening extending transversely to said inner surface means for circumbscribing a portion of the rod;

said clamp portion for clamping engagement with the rod upon tightening of the fastener against said base portion.

10. A clamp as set forth in claim 9 wherein said inner surface means of said clamp portion includes an arcuate wall for extending at least partially around the rod, said arcuate wall having first and second end portions which are disposed adjacent to each other, said base portion including a first leg section extending outwardly from said first end portion of said arcuate wall, a second leg section extending outwardly from said second end portion of said arcuate wall and disposed in a side-by-side relationshp with said first leg section, said surface means defining an opening in said base portion including a first surface extending through said first leg section to form a first opening and a second surface extending through said second leg section to form a second opening, said first and second openings being disposed in a coaxial relationship.

11. A clamp as set forth in claim 10 wherein said arcuate wall includes a first arcuate section connected with said first leg section and a second arcuate section connected with said second leg section and separate from said first arcuate section, said first arcuate section of said arcuate wall and said first leg portion for engagement with a vertebra, said second arcuate section of said wall and said second leg section being formed separately from said first arcuate section of said wall and said first leg section and being spaced from the vertebra.

12. A clamp as set forth in claim 11 wherein one of said arcuate sections of said arcuate wall has an inwardly projecting tang portion for extending into a notch in the rod disposed transversely to the longitudinal central axis of the rod to prevent rotational and axial movement of the rod relative to said clamp portion.

13. A clamp as set forth in claim 10 wherein said arcuate wall and said first and second leg sections are formed as one piece.

* * * * *

REEXAMINATION CERTIFICATE (2709th)

United States Patent [19]
Steffee

[11] B1 4,719,905
[45] Certificate Issued Oct. 31, 1995

[54] APPARATUS AND METHOD FOR MAINTAINING VERTEBRAE IN A DESIRED RELATIONSHIP

[75] Inventor: Arthur D. Steffee, Moreland Hills, Ohio

[73] Assignee: AcroMed Corp., Cleveland, Ohio

Reexamination Request:
No. 90/003,382, Mar. 31, 1994

Reexamination Certificate for:
Patent No.: 4,719,905
Issued: Jan. 19, 1988
Appl. No.: 936,314
Filed: Dec. 1, 1986

Related U.S. Application Data

[63] Continuation of Ser. No. 793,901, Nov. 1, 1985, Pat. No. 4,648,388.

[51] Int. Cl.⁶ ............................. A61F 5/04; A61B 17/70
[52] U.S. Cl. .................................................................. 606/61
[58] Field of Search .................................... 606/61, 99

[56] References Cited

U.S. PATENT DOCUMENTS 4,169,470  10/1979  Ender et al. ............................. 606/99
4,653,481  3/1987  Howland et al. .

*Primary Examiner*—Tamara L. Craysay

[57] ABSTRACT

An apparatus and method is provided to maintain vertebrae in a desired relationship. The apparatus includes a rod, a plurality of clamps, and a plurality of fastener assemblies. The method invovles inserting threaded members into openings in a displaced vertebra and at least one vertebra on each side of the displaced vertebra. A clamp is placed on each fastener. The rod is bent to correspond to a desired spinal curvature and inserted into the clamps. A nut is tightened on each threaded member to hold the clamp to each verebra and to press the clamp against the rod to hold the rod against axial and rotational movement.

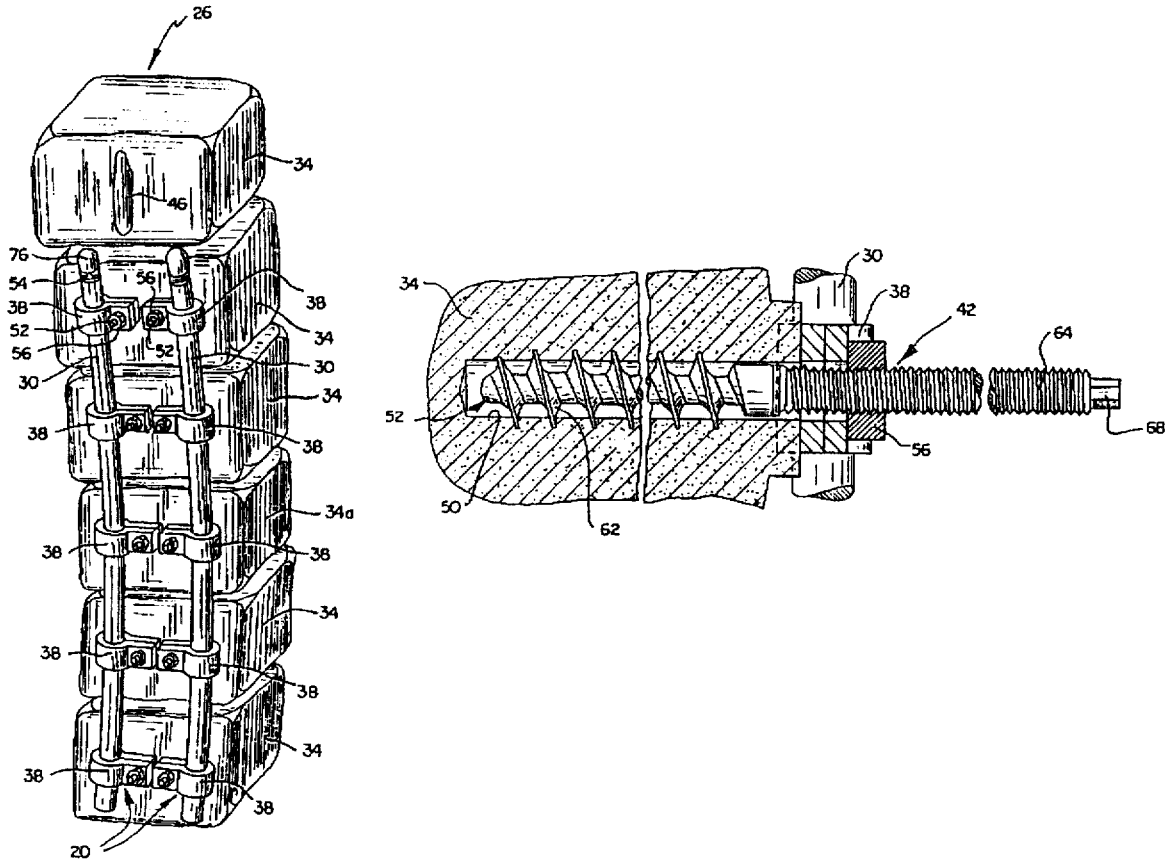

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 59–68:

Once the rods 30 have been plastically deformed or bent to the desired shape, they are inserted into clamps 38 which are held on the vertebrae by fastener assemblies 42. The fastener assemblies 42 are tightened, which presses the clamp 38 against the rod 30 to prevent the rod from rotational or axial movement. The position of the rod 30 can be adjusted, if so desired, by loosening the fastener assemblies 42. Once this has been done, the rods are moved to the desired position *which rotates the clamps 38 relative to the fastener assemblies 42 to position the clamps in any one of a plurality of positions relative to the fastener assemblies.* The fastener assemblies are retightened to again firmly grip the rod.

Column 4, lines 28–41:

The one-piece clamp 38 (FIG. 5) holds a rod 30 against rotational and axial movement relative to a vertebra. The one-piece clamp 38 has a base portion 84 and a clamp portion 86. The base portion 84 has two legs 88 extending from the clamp portion 86. The legs 88 are slightly spaced apart and the clamp portion 86 has a small resilient force acting to keep the legs spaced. Each of the legs 88 has a circular opening 90 for receiving the force transmitting member 52. *The openings 90 permit rotation of the clamp 38 relative to the force transmitting member 52 to position the clamp in any one of a plurality of positions relative to the fastener assembly 42 when the nut 56 is loose on the force transmitting member.* The clamp portion 86 (FIG. 5a) has an arcuate wall inner surface 92 of a generally cylindrical configuration extending around most of the rod 30 for engaging and clamping a portion of the rod which is disposed in the clamp 38. The legs 88 extend from end portions of the inner surface 92.

Column 4, lines 61–66:

A two-piece clamp 100 is illustrated in FIG. 6. The two-piece clamp 100 is made up of halves 102 and 104. Each half 102 or 104 has a base portion 106 and a clamp portion 108. The base portion 106 of each half 102 or 104 has an opening 110 for receiving the force transmitting member 52. *The openings 110 permit rotation of the clamp 100 relative to the force transmitting member 52 to position the clamp in any one of a plurality of positions relative to the fastener assembly 42 when the nut 56 is loose on the force transmitting member.*

AS A RESULT OF REEXAMINATION, IT HAS BEEN DETERMINED THAT:

Claims 8–10 are cancelled.

Claims 1, 4, 11 and 13 are determined to be patentable as amended.

Claims 2, 3, 5–7 and 12, dependent on an amended claim, are determined to be patentable.

1. An apparatus for maintaining a vertebrae in a desired relationship, said apparatus comprising:

a rod, said rod being deformable to a configuration which is a function of a desired curvature of a spine, said rod having sufficient length and rigidity to maintain the vertebrae in the desired relationship;

clamp means for gripping a portion of said rod, said clamp means having a clamp portion which includes inner surfaces which circumscribe said rod, said clamp means also having a base portion projecting outwardly from one side of said clamp portion, said base portion includes surface means defining an opening which is offset to one side of said rod;

fastener means for securing said clamp means to a vertebra and for pressing said inner surfaces of said clamp means against an outer side surface of said rod to hold said rod against axial and rotational movement relative to said clamp means, said fastener means including an externally threaded member extending through the opening in said base portion and having a central axis extending transversely to a central axis of said rod, said externally threaded member including threads for engaging a vertebra disposed on a first side of said clamp means; *and*

*said surface means defining the opening in said base portion including* [means for permitting rotation of said clamp means relative to said fastener] *threaded member* [while said threaded member extends through the opening in said base portion] *and said fastener means is in a loosened condition to position said clamp means in any one of a plurality of positions relative to said threaded member.*

4. An apparatus as set forth in claim 1 wherein said clamp portion of said clamp means includes an arcuate wall for extending at least part way around said rod, said arcuate wall having first and second end portions which are disposed adjacent to each other and are offset to one side of said rod, said base portion of said clamp means including a first leg section extending outwardly from said first end portion of said arcuate wall, a second leg section extending outwardly from said second end portion of said arcuate wall and disposed in a side-by-side relationship with said first leg section, said surface means defining [an] *the* opening in said base portion including a first surface extending through said first leg section to form a first opening and a second surface extending through said second leg section to form a second opening, said first and second openings being disposed in a coaxial relationship.

11. [A clamp as set forth in claim 10 wherein] *A clamp for use with an apparatus for maintaining vertebrae in a predetermined relationship wherein the apparatus includes at least one fastener for securing the clamp to a vertebra and a cylindrical rod, said clamp comprising:*

*a clamp portion having inner surface means for circumscribing a portion of the rod; and* a base portion extending from said clamp portion and having surface means defining an opening through said base portion for receiving the fastener, said opening extending transversely to said inner surface means for circumscribing a portion of the rod, said surface means defining said opening including means for permitting rotation of said clamp relative to the fastener when the fastener is in a loosened condition to position said clamp in any one of a plurality of positions relative to the fastener;

said clamp portion for clamping engagement with the rod upon tightening of the fastener against said base portion;

said inner surface means of said clamp portion including an arcuate wall for extending at least partially around the rod, said arcuate wall having first and second end portions which are disposed adjacent to each other, said base portion including a first leg section extending outwardly from said first end portion of said arcuate wall, a second leg section extending outwardly from said second end portion of said arcuate wall and disposed in a side-by-side relationship with said first leg section, said surface means defining the opening in said base portion including a first surface extending through said first leg section to form a first opening and a second surface extending through said second leg section to form a second opening, said first and second openings being disposed in a coaxial relationship;

said arcuate wall [includes] *including* a first arcuate section connected with said first leg section and a second arcuate section connected with said second leg section and separate from said first arcuate section, said first arcuate section of said arcuate wall and said first leg portion for engagement with a vertebra, said second arcuate section of said wall and said second leg section being formed separately from said first arcuate section of said wall and said first leg section and being spaced from the vertebra.

13. [A clamp as set forth in claim 10 wherein] *A clamp for use with an apparatus for maintaining vertebrae in a predetermined relationship wherein the apparatus includes at least one fastener for securing the clamp to a vertebra and a cylindrical rod, said clamp comprising:*

*a clamp portion having inner surface means for circumscribing a portion of the rod; and*

*a base portion extending from said clamp portion and having surface means defining an opening through said base portion for receiving the fastener, said opening extending transversely to said inner surface means for circumscribing a portion of the rod, said surface means defining said opening including means for permitting rotation of said clamp relative to the fastener when the fastener is in a loosened condition to position said clamp in any one of a plurality of positions relative to the fastener;*

*said clamp portion for clamping engagement with the rod upon tightening of the fastener against said base portion;*

*said inner surface means of said clamp portion including an arcuate wall for extending at least partially around the rod, said arcuate wall having first and second end portions which are disposed adjacent to each other, said base portion including a first leg section extending outwardly from said first end portion of said arcuate wall, a second leg section extending outwardly from said second end portion of said arcuate wall and disposed in a side-by-side relationship with said first leg section, said surface means defining the opening in said base portion including a first surface extending through said first leg section to form a first opening and a second surface extending through said second leg section to form a second opening, said first and second openings being disposed in a coaxial relationship;* said arcuate wall and said first and second leg sections [are] *being* formed as one piece.

* * * * *